United States Patent [19]

Berthel et al.

[11] Patent Number: 4,561,018
[45] Date of Patent: Dec. 24, 1985

[54] APPARATUS FOR CONTINUOUSLY INSPECTING THE PHYSICAL CHARACTERISTICS OF PARTICULATE MATTER

[75] Inventors: Robert O. Berthel, Windham, N.H.; Vernon G. Plank, Mansfield; Dennis L. LaGross, Bedford, both of Mass.

[73] Assignee: The United States of America as represented by the Secretary of the Air Force, Washington, D.C.

[21] Appl. No.: 442,493

[22] Filed: Nov. 18, 1982

[51] Int. Cl.⁴ .............................................. H04N 7/18
[52] U.S. Cl. .................................... 358/107; 358/100; 250/222.2; 250/223 R
[58] Field of Search ................... 358/93, 100, 101, 106, 358/107, 108, 229, 227; 250/222.2, 223 R, 239; 356/36; 73/432 PS

[56] References Cited

U.S. PATENT DOCUMENTS

| | | | |
|---|---|---|---|
| 417,357 | 12/1889 | Fergusson . | |
| 1,877,713 | 12/1929 | Beck . | |
| 2,524,926 | 4/1948 | Peery | 88/14 |
| 2,721,495 | 3/1952 | Schaefer | 88/14 |
| 2,954,690 | 3/1958 | Dickinson | 73/171 |
| 3,275,744 | 10/1962 | Dietrich | 178/6 |
| 3,390,229 | 11/1962 | Williams | 178/6 |
| 3,475,965 | 3/1968 | Koblin et al. | 73/432 |
| 3,589,813 | 1/1968 | Sturzinger | 356/72 |
| 3,614,231 | 2/1968 | Shaw | 356/37 |
| 3,801,779 | 4/1974 | Ver Sluis | 250/222 |
| 3,914,053 | 10/1975 | Morley et al. | 356/37 |
| 4,035,635 | 7/1977 | Crosland et al. | 250/223 R |
| 4,070,575 | 1/1978 | Park et al. | 250/223 R |
| 4,136,950 | 1/1979 | Labrum et al. | 358/107 |
| 4,162,509 | 7/1979 | Robertson | 356/28 |
| 4,179,704 | 12/1979 | Moore et al. | 358/22 |
| 4,305,658 | 12/1981 | Yoshida | 356/23 |

FOREIGN PATENT DOCUMENTS 2012948  8/1979  United Kingdom ............ 73/432 PS

Primary Examiner—Edward L. Coles, Sr.
Attorney, Agent, or Firm—Donald J. Singer; Jacob N. Erlich

[57] ABSTRACT

An apparatus for continuously inspecting the physical characteristics of particulate matter having a collection and conveying system, a sampling compartment, and a camera system. The collection and conveying system transports particulate matter, in the form of snowflakes, for example, to a viewing area in the sampling compartment. The camera system monitors the viewing area in order to provide single or multiple images of the snowflakes on single video frames at suitable magnification in order to analyze the crystalline characteristics of the snowflakes under naturally occurring conditions.

16 Claims, 5 Drawing Figures

APPARATUS FOR CONTINUOUSLY INSPECTING THE PHYSICAL CHARACTERISTICS OF PARTICULATE MATTER

STATEMENT OF GOVERNMENT INTEREST

The invention described herein may be manufactured and used by or for the Government for governmental purposes without the payment of any royalty thereon.

BACKGROUND OF THE INVENTION

This invention relates generally to devices capable of viewing particulate matter, and, more particularly, to an apparatus which is capable of continuously inspecting snowflakes in order to determine the physical characteristics of their crystalline structure.

It has long been recognized that electro-optical and communications systems are especially susceptible to attenuation because of falling snow. In addition to falling snow, other types of hydrometeors or particulate matter can have an adverse affect on electro-optical and microwave systems as well as other communications systems. Therefore, it becomes extremely important to study the characteristics of the crystalline structure of certain types of hydrometeors such as snow or ice and to relate their particular crystalline forms with changes in electromagnetic attenuation, fall velocity, density, etc. In addition, the viewing of such hydrometeors should take place in the field and under the exact conditions in which such hydrometeors such as snowflakes or ice actually affect the operation of electro-optical, microwave and communication systems.

Heretofore, devices which were utilized to provide such visual observations were lacking in some of the above-mentioned desirable features. For example, their operation in the field, in many instances, was subject to unpredictable and/or unreliable operation. In addition, past devices did not provide sufficient visualization of the exact crystalline structure of such hydrometeors as snowflakes or ice in a continuous fashion and in a highly accurate manner.

It is therefore clearly evident that it is highly desirable to provide an apparatus which is capable of continuously inspecting the physical characteristics of snowflakes, in particular, or any other types of particulate matter, in general.

SUMMARY OF THE INVENTION

The apparatus for continuously inspecting the physical characteristics of particulate matter (hereinafter referred to as the inspection apparatus) of the present invention is made up of three major components; (1) a particulate matter collecting and conveying system, (2) a sampling compartment, and (3) a camera system.

The collecting and conveying system includes a moving belt for capturing the particulate matter which in most instances is in the form of snowflakes or ice particles. The particulate matter is then transported into a viewing area in the sampling compartment wherein it is appropriately illuminated. A conventional video camera, which forms part of the camera system, continuously monitors the snowflakes or ice particles positioned within the sampling compartment.

Illumination within the sampling compartment may take the form of a strobe lighting unit of specified frequency which combines with a conveyor of pre-set speed. In place of the strobe lighting unit, a pair of incandescent lamps may be utilized in conjunction with a Geneva gear drive conveyor. This type of drive is preferred over a stepping motor since it has smoother action and will not shock the particulate matter of the conveyor belt. Observation of the monitored snowflakes or ice particles can be made by means of by appropriate video camera and its associated conventional television. Information can be subsequently recorded on a video tape.

The entire collecting and conveying system, sampling compartment, and camera system is enclosed in a sheet-metal housing which contains an adjustable opening therein for regulated particle entry. The protective housing is generally maintained at ambient temperature in the area of the conveying and collecting system and sampling compartment while a suitable heater element may be utilized in conjunction with the camera system in order to maintain the video camera under ideal operating temperatures. In certain instances, it may be desirable to provide a heating device in the sampling compartment as well in order for studies to be made of snow flake or ice particle melting.

In addition, the makeup of the conveyor would be such that it will not disturb the crystalline structure of a falling snowflake or ice particle. Therefore, the conveyor must not only be made of a non-absorbent material, but must also provide a sufficient cushioning effect on the falling snow. Furthermore, the interior surface of the conveyor is slotted to accommodate a gear drive to provide for positive and accurate movement of the conveyor.

The inspection apparatus of the present invention is also capable of being used for other types of particulate matter. In any use, the present invention is capable of providing a greatly magnified image of the particular matter which can be displayed on a television or video screen and subsequently recorded on video tape. Thus, observation of crystalline types can be made over any time extent. Measurements of various sizes can also be made using the image of a removable plastic grid to adjust for magnification.

It is therefore an object of this invention to provide an inspection apparatus capable of continuously recording the crystalline structure of individual particles of snow and/or ice.

It is another object of this invention to provide an inspection apparatus which is capable of substantially magnifying the individual particulate matter under investigation in order to enable identification of its crystalline structure.

It is still a further object of this invention to provide an inspection apparatus which is capable of directly viewing the particulate matter under investigation and recording information with respect thereto without further intermediate processing.

It is still another object of this invention to provide an inspection apparatus which is economical to produce and which utilizes conventional, currently available components that lend themselves to standard mass producing manufacturing techniques.

For a better understanding of the present invention, together with other and further objects thereof, reference is made to the following description taken in conjunction with the accompanying drawing and its scope will be pointed out in the appended claims.

DETAILED DESCRIPTION OF THE DRAWING

DETAILED DESCRIPTION OF THE PREFERRED EMBODIMENTS

Figure 1:
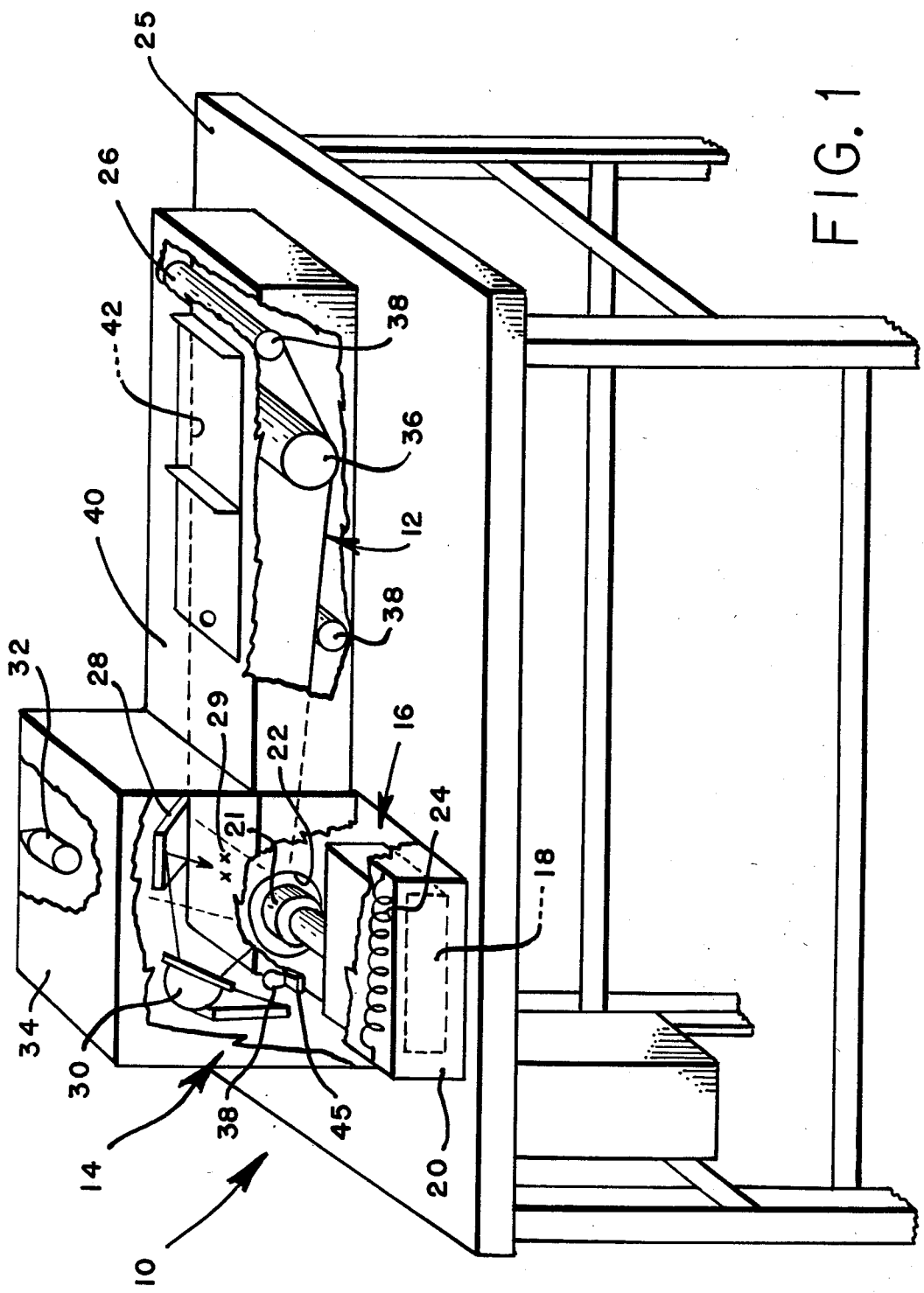
FIG. 1 is a pictorial representation, shown in partly segmented fashion, of the inspection apparatus of this invention.

Reference is now made to FIG. 1 of the drawing which clearly depicts in pictorial fashion the apparatus of the present invention for continuously inspecting the physical characteristics of particulate matter and which will be hereinafter referred to as inspection apparatus 10 of this invention. Inspection apparatus 10 is made up of three major components; (1) a particulate matter collecting and conveying system 12, (2) a sampling compartment 14, and (3) a camera system 16.

More specifically, camera system 16 includes a conventional video camera 18 such as RCA Model TC 1005/01 Vidicon located within a temperature controlled enclosure 20. The lens 21 (preferably a zoom-type magnification lens such as Fuji optical model 1:18/16-160 TV Zoom) on video camera 18 is aimed through an opening 22 formed between enclosure 20 of camera system 16 and the housing surrounding sampling compartment 14. The video camera 18, which is located within enclosure 20, is electrically heated by any conventional heater element 24 situated therein. Heater element 24 maintains a proper operating temperature within enclosure 20 for camera 18 even though the entire inspection apparatus 10 is situated outdoors and in less than desirable temperature conditions. The inspection apparatus 10 may be mounted upon a rigid support table 25 for accurate placement of the inspection apparatus 10 while in use in the field.

Adjacent the camera system 16 is the sampling compartment 14 into which passes a portion of the conveyor 26 of the collection and conveying system 12 which will be described in greater detail hereinbelow. Located in sampling compartment 14 and adjacent conveyor 26 and optically aligned with camera 18 is a suitable angled reflecting element 28. In the embodiment illustrated in FIG. 1 of the drawing illumination of particulate matter 29 brought into the sampling compartment 14 by conveyor 26 is provided by means of a conventional strobe lamp 30 such as General Radio Model GR 1538-A mounted in a position removed from yet adjacent conveyor 26.

Light provided by strobe lamp 30 directly illuminates particulate matter 29 in the form of a snowflake or ice particle. In addition, reflected light from reflecting element 28 indirectly illuminates the snowflake. The alignment of reflecting element 28 insures that camera 18 will receive an image of the snowflake or ice particle from above. Although, generally the sampling compartment 14 remains unheated, in some instances a heater such as an infrared lamp 32 may be utilized in conjunction therewith if, for example, the snowflake or ice particle is to be studied during the melting thereof. Sampling compartment 14 is preferably encased by a housing 34 which is made, for example, of sheet metal and is painted in an absorbent color such as flat back. As stated above an aperture 22 is provided adjacent camera 18 so as to allow for the viewing of the particulate matter by camera 18.

Introduction of the particulate matter 29 to the sampling compartment 14 is accomplished by means of a collection and conveying system 12 which generally includes conveyor 26 mounted upon a driving gear 36 and a plurality of rollers 38. In general, a conventional drive motor (not shown) and suitable gear reduction mechanisms are used to move conveyor 26 along its predetermined path at a predetermined rate of speed of, for example, 2.5 cm per second.

Conveyor 26 must be made of a material which is nonabsorbent and in addition provides a cushioning effect for the falling snowflake or ice particle. Such a conveyor 26 may therefore be made of a rubber, reinforced fiber filament belt in order to prevent any damage from occurring to the collected snowflake or ice particle. The interior surface of the belt of conveyor 26 is slotted so as to accept the teeth of gear driving element 36 for positive movement of conveyor 26.

Figure 2:
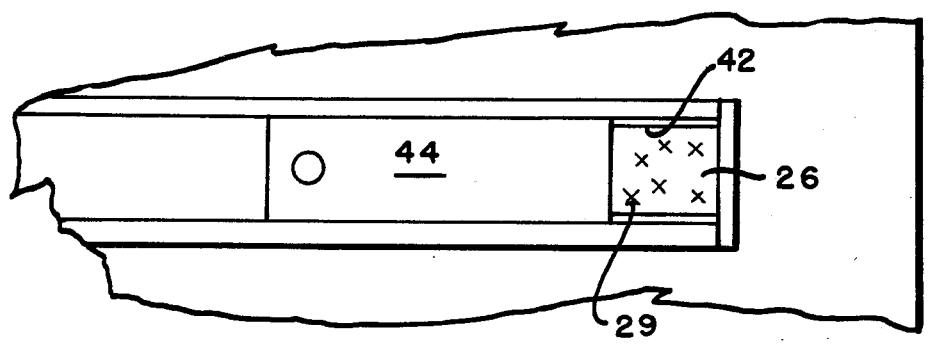
FIG. 2 is a top view of the adjustable port of the inspection apparatus of this invention.

Conveyor 26 of collection and conveying system 12 is enclosed in a sheet metal housing 40, preferably having an absorbant colored interior of, for example, flat back. Cut into the top portion of housing 40 is a rectangular shaped collection port 42, more clearly illustrated in FIG. 2 of the drawing. The size of port 42 may be varied by means of an adjustable sliding shutter-like element 44 which by the manual movement thereof can accurately vary the size of port 42. Snowflakes or ice crystals entering port 42 are deposited directly onto the moving conveyor 26 and thereby transported into the viewing area of sampling compartment 14 for subsequent observation and monitoring. As stated hereinabove, mirror 28 which is angled at preferably 45° and mounted across the belt in order to allow viewing of the snowflakes or ice crystals as they pass by.

Referring once again to sampling compartment 14, the positioning of the strobe lamp 30 as well as mirror 28 allows for the minimization of interfacing between the particles on conveyor 26 and therefore allows for a clear and unobstructed view thereof by camera 18. As conveyor 26 continues over the last roller 38 in the viewing area of sampling compartment 14 a scraper-like element 45 is located adjacent thereto and removes any of the snowflakes or ice crystals which remain upon conveyor 26 so that subsequent movement of conveyor 26 back to collection port 42 will provide a clean surface for further collection and subsequent observation.

As stated hereinabove the captured or deposited snowflakes or ice particles are transferred into the field of view of the video camera 18. Video camera 18 is equipped with a magnifying lens 21 and the imges are recorded on a video tape. The particle images received are actually reflected by the 45° mirror 28. Such an arrangement enables video camera 18 and its associated heated enclosure 20 to be in a horizontal position and not obstruct either the viewing area or the falling snow. The lighting which has been provided by strobe lamp 30 has its frequency adjusted with respect to the conveyor speed in order to provide a single or multiple images of the particulate matter on single video frames.

Figure 3:
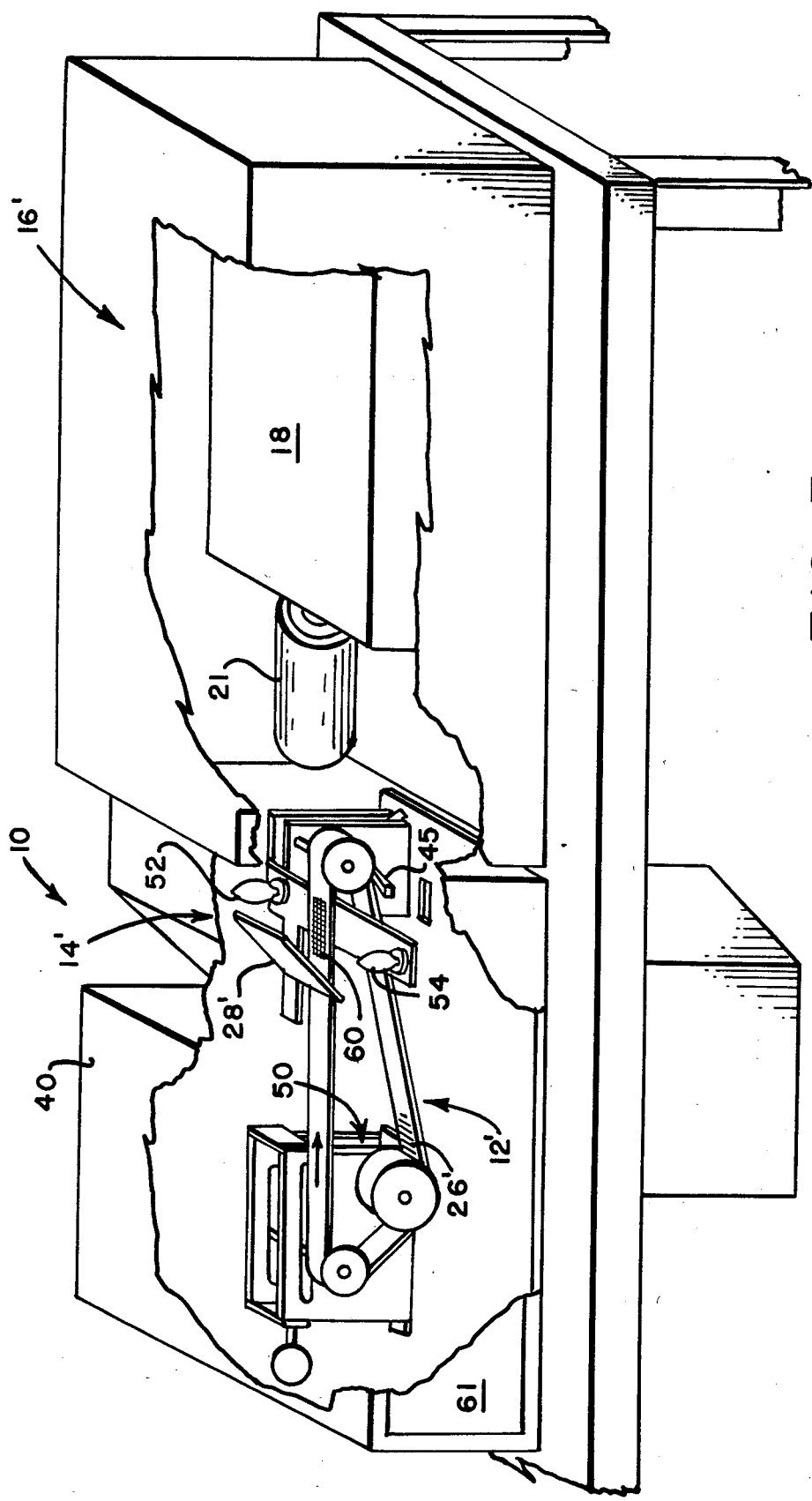
FIG. 3 is a pictorial representation, shown in partly segmented fashion, of an alternate embodiment of the inspection apparatus of this invention.

It has been found under certain circumstances that the utilization of a strobe lamp 30 as illustrated with respect to FIG. 1 of the drawing may provide a slight degree of blurring of the observed snowflake or ice particle. In order to overcome this slight deficiency with the embodiment illustrated in FIG. 1 of the drawing, an alternative embodiment of the inspection apparatus 10 of the present invention is illustrated in FIG. 3 of the drawing as inspection apparatus 10'. Since the major components of each embodiment, that is, (1) the camera system, (2) the sampling compartment, and (3) the collection and conveying system are of substantially identical elements, the same reference numerals will be used to designate identical elements of both embodiments. In addition, since the concepts involved in both embodiments are substantially identical much of the detailed operation of the present invention described with respect to the embodiment of FIG. 1 will be omitted when describing the alternate embodiment of inspection apparatus 10' set forth in FIG. 3 of the drawing.

Figure 4:
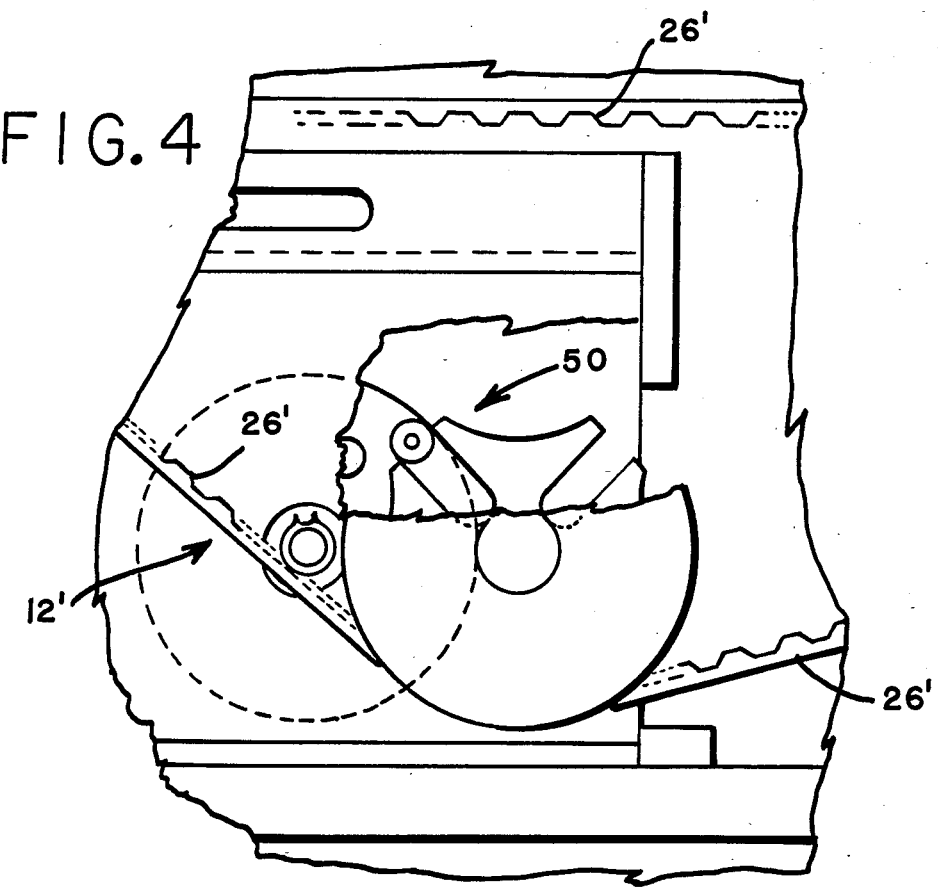
FIG. 4 is a side elevational view, shown in partly segmented fashion, of the Geneva drive used with the alternate embodiment of the inspection apparatus of this invention.

The major difference between inspection apparatus 10' and inspection apparatus 10 illustrated in FIGS. 3 and 1, respectively, involves the design of collection and conveying system 12' (see FIG. 3). Collection and conveying system 12' incorporates therein a Geneva drive 50 (clearly illustrated in FIG. 4 of the drawing) in combination with a pair of incandescent lamps 52 and 54 located within sampling compartment 14'. The camera system 16' is identical to that utilized with respect to inspection apparatus 10 set forth in FIG. 1 of the drawing except that it is located directly in line with (or parallel to) conveyor 26'. Consequently, the incandescent lamps 52 and 54 located within sampling compartment 14' are situated on opposite sides of conveyor 26'. The angled reflector or mirror 28' is situated intermediate incandescent lamps 52 and 54 and above conveyor 26'. As with respect to the inspection apparatus 10 illustrated in FIG. 1, mirror 28' is positioned at approximately 45° with respect to the horizontal. The opening 22' between the sampling compartment 14' and the camera system 16' is therefore located at the end of sampling compartment 14' and in line with camera 18 for observation and monitoring of particulate matter being collected and conveyed by conveyor 26'.

The utilization of a Geneva driven conveyor 26' eliminates any problems with respect to blurring images and this type of drive mechanism is preferred over a stepping motor since it is capable of providing extremely smooth action and will not shock the particles located on conveyor 26'. Illumination of the particulate matter within sampling compartment 14' is provided by incandescent lamps 52 and 54 of, for example, 6 watt intensity. The speed of the belt making up conveyor 26' could be approximately 2.5 cm per second with a designed criteria of belt movement of approximately 4 cm with each step. The stationary time would be approximately 1.5 seconds. These values, however, can be varied by changes in the gear ratio and/or the motor speed. All other components of the alternate embodiment of inspection apparatus 10' of the present invention would be similar to those shown with respect to inspection apparatus 10 illustrated in FIG. 1. For example, an adjustable collection port would be formed in housing 40, even though this port is not illustrated in FIG. 3 of the drawing.

Figure 5:
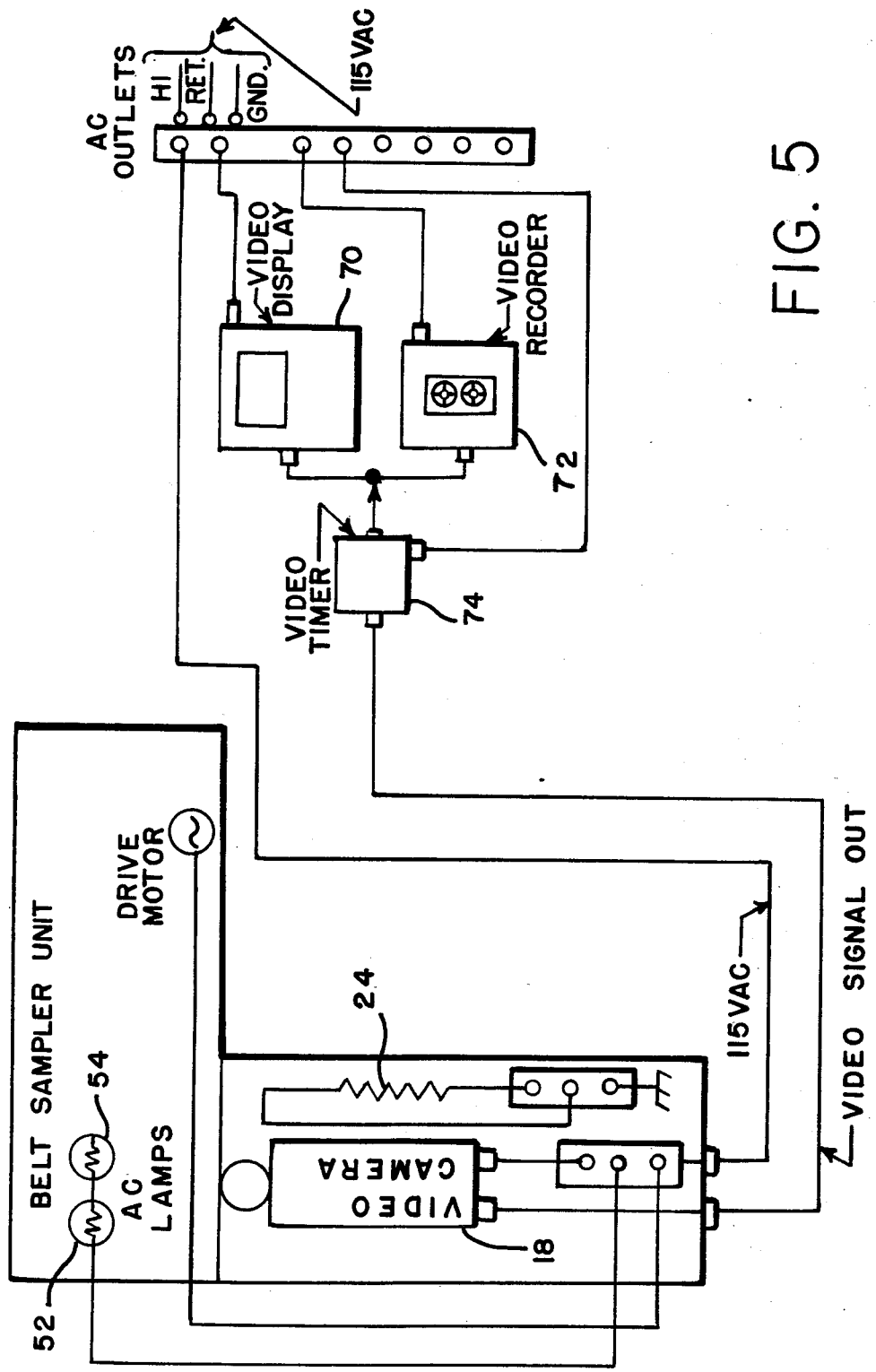
FIG. 5 is a schematic representation of the various electrical components of the alternate embodiment of the inspection apparatus of this inventon.

Reference is now made to FIG. 5 of the drawing which illustrates the various electrical components that make up inspection apparatus 10' of this invention. The electrical components include a TV monitor or video display 70, a video cassette recorder 72 and a video counter/timer 74. The timer 74 provides the video frame count to both the TV monitor or display 70 and the cassette recorder 72.

MODE OF OPERATION

During operation with either of the embodiments of the inspection apparatus 10 or 10' illustrated in either FIGS. 1 and/or 3 of the drawing, snowflakes or ice particles fall through the port 42 after port 42 has been adjusted to a predetermined size and onto conveyor 26 or 26'. Since the conveyor 26 or 26' is of a non-wettable or nonabsorbent material these snowflakes will remain in an unaltered state for transfer into the sampling compartment 14 or 14'. The captured snowflakes or ice particles are transferred into the field of view of the video camera 18 where they are viewed in a stopped position as a result of the timed strobe lamp 30 or Geneva drive 50 associated with conveyor 26'. Monitoring thereof takes place by means of video camera 18. Since the particle images are actually reflected by mirror 28 or 28', the camera 18 does not obstruct either the falling snowflakes or the observation of the snowflakes.

A detailed analysis can be made of the crystalline structure of the snowflakes or ice particles by a high magnification of the particle itself by means of the zoom lens 21 associated with camera 18. A removable grid 60 can be placed upon a portion of the conveyor adjacent camera 18 prior to actual collection and conveying of the particles through an access door 61 (shown in FIG. 3) in order to serve to calibrate the overall optical system for the magnification of the optical system. This allows for accurate and reliable analysis of crystalline structure.

Even though the inspection apparatus 10 and 10' of the present invention is primarily used for the analysis of snowflakes and/or ice particles, it may be used for other types of particulate matter when it is necessary to study these types of particulate matter at close range and under greater magnification than occurs when the matter is under a naturally falling condition.

Although this invention has been described with reference to a particular embodiment, it will be understood that this invention is also capable of further and other embodiments within the spirit and scope of the appended claims.

We claim:

1. An inspection apparatus for continuously viewing the physical characteristics of particulate matter, comprising:

means for collecting said particulate matter and conveying said particulate matter to a preselected area, with said particulate matter remaining on said collecting and conveying means at said preselected area;

means situated adjacent said preselected area for providing sufficient illumination of said particulate matter at said preselected area and for providing an image of said particulate matter from above;

means optically aligned with said image of said particulate matter for monitoring said particulate matter and providing signals representative thereof; and means operably connected to said monitoring means for receiving said signals and providing a display of said particulate matter at a preselected magnification.

2. An inspection apparatus for continuously viewing the physical characteristics of particulate matter as defined in claim 1 wherein said collecting and conveying means and said illuminating means cooperate together in order to provide single or multiple images of said particulate matter on single video frames.

3. An inspection apparatus for continuously viewing the physical characteristics of particulate matter as defined in claim 2 wherein said collecting and conveying means comprises a conveyor belt made of a nonabsorbent, cushioned material, and means for moving said conveyor at a preselected rate of speed.

4. An inspection apparatus for continuously viewing the physical characteristics of particulate matter as defined in claim 3 wherein said means for moving said conveyor belt at a preselected speed comprises a Geneva drive gear mechanism capable of stopping said conveyor belt for preselected periods of time.

5. An inspection apparatus for continuously viewing the physical characteristics of particulate matter as defined in claim 3 wherein said illumination means comprises a strobe lamp, said strobe lamp having a preselected frequency of illumination.

6. An inspection apparatus for continuously viewing the physical characteristics of particulate matter as defined in claim 4 wherein said illumination means comprises at least one continuous means of illumination.

7. An inspection apparatus for continuously viewing the physical characteristics of particulate matter as defined in claim 5 wherein said means for providing an image of said particulate matter from above comprises a reflecting element positioned at a preselected angle adjacent said conveyor belt.

8. An inspection apparatus for continuously viewing the physical characteristics of particulate matter as defined in claim 6 wherein said means for providing an image of said particulate matter from above comprises a reflecting element positioned at a preselected angle adjacent said conveyor belt.

9. An inspection apparatus for continuously viewing the physical characteristics of particulate matter as defined in claim 7 further comprising means for removing said particulate matter from said conveyor belt after monitoring thereof has taken place.

10. An inspection apparatus for continuously viewing the physical characteristics of particulate matter as defined in claim 8 further comprising means for removing said particulate matter from said conveyor belt after monitoring thereof has taken place.

11. An inspection apparatus for continuously viewing the physical characteristics of particulate matter as defined in claim 9 wherein said monitoring means is located within an enclosure, said enclosure having a controllable heat source therein.

12. An inspection apparatus for continuously viewing the physical characteristics of particulate matter as defined in claim 10 wherein said monitoring means is located within an enclosure, said enclosure having a controllable heat source therein.

13. An inspection apparatus for continuously viewing the physical characteristics of particulate matter as defined in claim 11 wherein said preselected area is enclosed in a housing, said housing having a controllable heat source therein.

14. An inspection apparatus for continuously viewing the physical characteristics of particulate matter as defined in claim 12 wherein said preselected area is enclosed in a housing, said housing having a controllable heat source therein.

15. An inspection apparatus for continuously viewing the physical characteristics of particulate matter as defined in claim 13 further comprising a removable grid for calibrating said apparatus for the magnification of said particulate matter.

16. An inspection apparatus for continuously viewing the physical characteristics of particular matter as defined in claim 14 further comprising a removable grid for calibrating said apparatus for the magnification of said particulate matter.

* * * * *